(12) United States Patent
Glaspie et al.

(10) Patent No.: US 12,251,084 B2
(45) Date of Patent: Mar. 18, 2025

(54) BIOPSY APPARATUS HAVING A SAMPLE COLLECTION CONTAINER

(71) Applicant: C. R. Bard, Inc., Franklin Lakes, NJ (US)

(72) Inventors: Koltin K. Glaspie, Chandler, AZ (US); Angela K. Jensen, Phoenix, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 1054 days.

(21) Appl. No.: 16/961,858

(22) PCT Filed: Feb. 8, 2018

(86) PCT No.: PCT/US2018/017366
§ 371 (c)(1),
(2) Date: Jul. 13, 2020

(87) PCT Pub. No.: WO2019/156669
PCT Pub. Date: Aug. 15, 2019

(65) Prior Publication Data
US 2020/0337684 A1    Oct. 29, 2020

(51) Int. Cl.
| | | |
|---|---|---|
| A61B 10/00 | (2006.01) | |
| A61B 10/02 | (2006.01) | |
| A61B 10/04 | (2006.01) | |
| A61B 10/06 | (2006.01) | |

(52) U.S. Cl.
CPC ...... *A61B 10/0096* (2013.01); *A61B 10/0275* (2013.01); *A61B 10/02* (2013.01); *A61B 2010/0208* (2013.01); *A61B 10/04* (2013.01); *A61B 2010/045* (2013.01); *A61B 10/06* (2013.01)

(58) Field of Classification Search
CPC . A61B 10/0096; A61B 10/0275; A61B 10/02; A61B 2010/0208; A61B 10/0283; A61B 2010/0225; A61B 10/04; A61B 10/06; A61B 2010/045
See application file for complete search history.

(56) References Cited

U.S. PATENT DOCUMENTS

| | | | |
|---|---|---|---|
| 4,697,600 A | 10/1987 | Cardenas et al. | |
| 4,795,481 A | 1/1989 | Ellis | |
| 5,575,293 A | 11/1996 | Miller et al. | |
| 5,609,827 A | 3/1997 | Russell et al. | |
| 6,551,834 B2 | 4/2003 | Carpenter et al. | |

(Continued)

FOREIGN PATENT DOCUMENTS

| | | |
|---|---|---|
| CN | 101578031 A | 11/2009 |
| CN | 103246157 A | 8/2013 |

(Continued)

OTHER PUBLICATIONS

Office Action dated Apr. 20, 2024 pertaining to CN 201880088869.2 filed Aug. 7, 2020.

*Primary Examiner* — Jennifer Robertson
*Assistant Examiner* — Jonathan Drew Moroneso
(74) *Attorney, Agent, or Firm* — Dinsmore & Shohl LLP (57) ABSTRACT

A sample collection container for a biopsy apparatus includes a sample capture body defining an interior space. The sample capture body is made of a fabric and has an interior sample capture surface that at least partially surrounds the interior space. The fabric has at least one fold.

16 Claims, 6 Drawing Sheets

(56) References Cited

U.S. PATENT DOCUMENTS

| | | | |
|---|---|---|---|
| 6,887,210 B2 | 5/2005 | Quay | |
| 7,942,896 B2* | 5/2011 | Anderhub | A61B 10/06 |
| | | | 606/207 |
| 8,163,252 B2 | 4/2012 | Booker et al. | |
| 8,329,474 B2 | 12/2012 | Fischer | |
| 9,173,641 B2* | 11/2015 | Chudzik | A61B 10/0275 |
| 2004/0255739 A1* | 12/2004 | Clifford | A61B 10/0266 |
| | | | 83/13 |
| 2007/0116612 A1 | 5/2007 | Williamson, IV | |
| 2008/0050805 A1 | 2/2008 | Cole et al. | |
| 2008/0077045 A1 | 3/2008 | Burbank et al. | |
| 2010/0152612 A1 | 6/2010 | Headley, Jr. et al. | |
| 2012/0203241 A1* | 8/2012 | Williamson, IV | A61B 10/06 |
| | | | 606/114 |
| 2014/0275999 A1 | 9/2014 | Speeg, V et al. | |
| 2014/0343453 A1* | 11/2014 | Waxler | A61B 10/0275 |
| | | | 600/564 |
| 2015/0018712 A1 | 1/2015 | Seiger et al. | |
| 2015/0277373 A1 | 10/2015 | Yamaguchi et al. | |
| 2016/0106399 A1* | 4/2016 | Gracias | A61B 10/0233 |
| | | | 600/562 |
| 2016/0183928 A1 | 6/2016 | Speeg, V et al. | |
| 2016/0338716 A1* | 11/2016 | Aslinia | A61B 17/10 |
| 2017/0079519 A1* | 3/2017 | Sung | A61B 8/12 |
| 2020/0390425 A1* | 12/2020 | Chaffringeon | A61F 13/15203 |

FOREIGN PATENT DOCUMENTS

| | | | | |
|---|---|---|---|---|
| CN | 103762112 B | 4/2014 | | |
| CN | 104941327 B | 9/2015 | | |
| FR | 2937024 A1 * | 4/2010 | | A61B 50/20 |
| WO | WO-2018119473 A1 * | 6/2018 | | A61B 10/02 |

\* cited by examiner

BIOPSY APPARATUS HAVING A SAMPLE COLLECTION CONTAINER

CROSS-REFERENCE TO RELATED APPLICATIONS

This application is a U.S. national phase of International Application No. PCT/US2018/017366, filed Feb. 8, 2018, which is incorporated herein by reference in its entirety.

TECHNICAL FIELD

The present invention relates to a biopsy apparatus for collecting tissue samples, and, more particularly, to a biopsy apparatus having a sample collection container.

BACKGROUND ART

A biopsy may be performed on a patient to help in determining whether the cells in a tissue lesion to be biopsied are cancerous. A typical biopsy apparatus may include a hand-held driver assembly and a disposable biopsy probe assembly configured for releasable attachment to the driver assembly. The biopsy probe assembly may include a biopsy stylet coaxial with a cutting cannula. The biopsy stylet may include a tubular member having a lumen, a distal piercing tip, and a sample port for receiving the tissue to be sampled. The cutting cannula may be a tubular member having a distal cutting edge, which is axially moved over the sample port for severing tissue received in the sample port. The hand-held driver assembly may include a vacuum source to move a severed tissue sample via vacuum to a sample reservoir. The sample reservoir may include a removable plastic sample container to collect the tissue samples. The sample container is interposed in a fluid path between the sample port of the biopsy stylet and the vacuum source. Accordingly, the sample container typically has a grid of vent holes to facilitate vacuum communication between the sample port of the biopsy stylet and the vacuum source, and in turn, to facilitate transport of the tissue sample from the sample port of the biopsy stylet to the sample container.

However, it has been observed that micro-calcifications may get stuck in the holes of the sample container. In such a case, additional efforts and imaging of the sample container are needed in order to ensure that the micro-calcifications were in fact biopsied and collected during the procedure. Imaging of the micro-calcification can be difficult with use of such a sample container because the samples can become stuck within the holes of the sample container. Moreover, there is the possibility for the micro-calcifications to pass through the holes of the sample container and be unavailable for diagnostic evaluation.

What is needed in the art is a biopsy apparatus having a sample collection container configured to capture all pieces of the tissue sample, including micro-calcifications.

SUMMARY OF INVENTION

The present invention provides a biopsy apparatus having a sample collection container configured to capture all pieces of the tissue sample, including micro-calcifications.

The invention in one form is directed to a sample collection container for a biopsy apparatus that includes a sample capture body defining an interior space. The sample capture body is made of a fabric and has an interior sample capture surface that at least partially surrounds the interior space. The fabric has at least one fold.

The invention in another form is directed to a biopsy apparatus that includes a driver assembly and a biopsy probe assembly. The driver assembly includes a housing having a proximal end. A vacuum source is contained within the housing. The biopsy probe assembly is releasably mounted to the housing. The biopsy probe has an elongate sample receiving member and a cutting cannula coaxial with the elongate sample receiving member. A sample receptacle is removably mounted to the proximal end of the housing. The sample receptacle is coupled in fluid communication with each of the biopsy probe assembly and the vacuum source. A sample collection container is removably carried by the sample receptacle. The sample collection container includes a sample capture body that defines an interior space. The sample capture body is made of a fabric and has an interior sample capture surface that at least partially surrounds the interior space. The fabric has at least one fold.

An advantage of the present invention is that the sample capture body can be unfolded to remove any tissue sample received by the sample capture body, and then refolded and reused to capture additional tissue samples, from the same patient.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DESCRIPTION OF EMBODIMENTS

Figure 1:
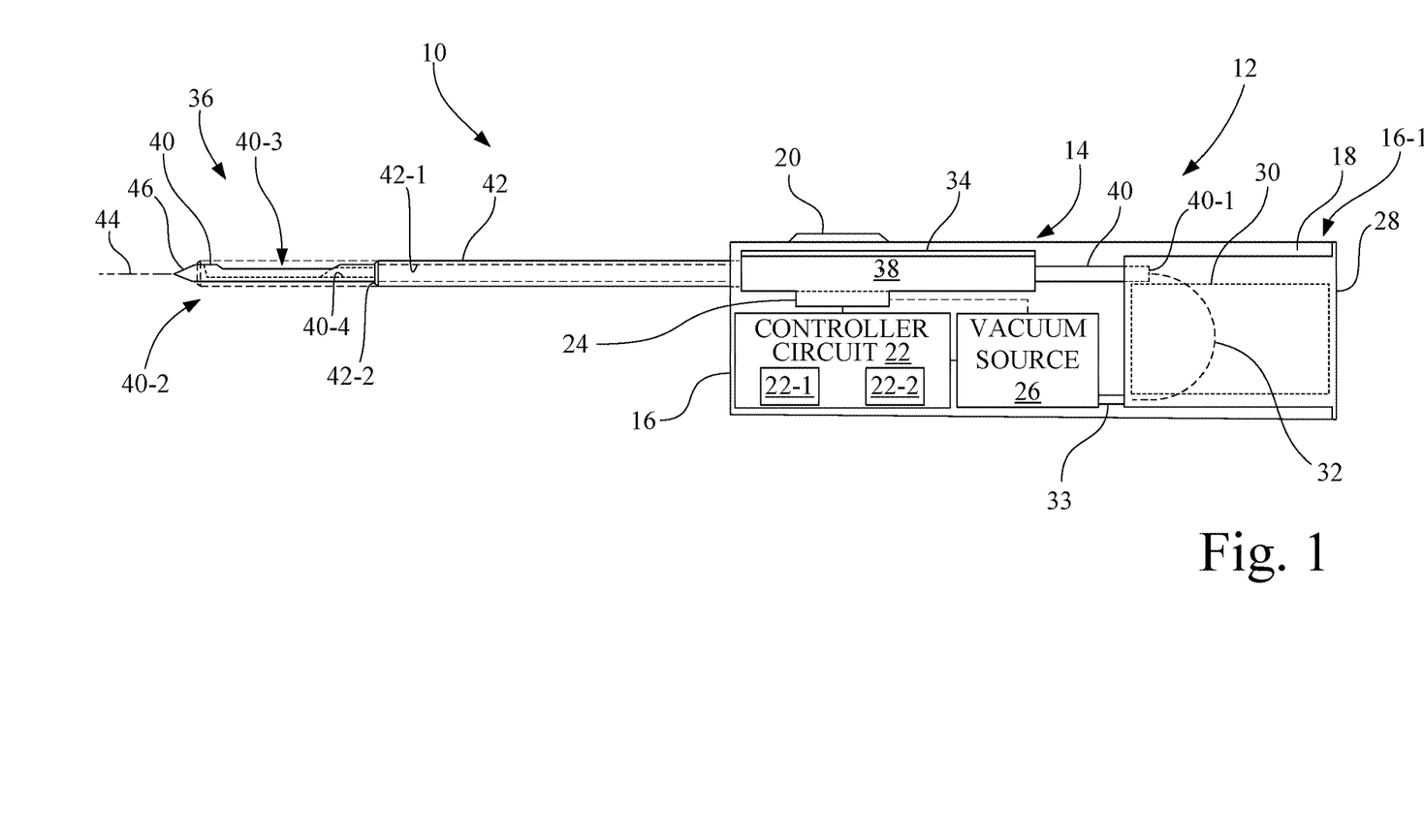
FIG. 1 is a diagrammatic representation of a biopsy apparatus having a sample collection container in accordance with an aspect of the present invention.

Referring now to the drawings, and more particularly to FIG. 1, there is shown a biopsy apparatus 10 configured in accordance with an embodiment of the invention.

Biopsy apparatus 10 includes a driver assembly 12 and a biopsy probe assembly 14. Driver assembly 12 is configured to provide operative control over biopsy probe assembly 14.

Driver assembly 12 has a housing 16 that is configured, e.g., ergonomically designed, to be grasped by a user, e.g., a physician. Housing 16 defines a compartment 18 into which biopsy probe assembly 14 is at least partially positioned when biopsy probe assembly 14 is attached to driver assembly 12, at which time biopsy probe assembly 14 is drivably coupled to driver assembly 12.

Driver assembly 12 includes a user interface 20, a controller circuit 22, an electromechanical drive 24, a vacuum source 26, and a sample receptacle 28. Each of controller circuit 22, electromechanical drive 24, and vacuum source 26 is contained within housing 16. Sample receptacle 28 is removably mounted to a proximal end 16-1 of housing 16, and extends distally into compartment 18. Sample receptacle 28 may be, for example, a removable tray that carries a removable sample collection container 30 that is configured in accordance with an aspect of the present invention.

User interface 20 is located to be externally accessible to the user with respect to housing 16. User interface 20 may be in the form of a touch screen display that is configured to receive operation commands from the user, e.g., through one or more pushbuttons, and to display visual indicators on a display, e.g., one or more lights, text and/or icons, to display information to the user.

Controller circuit 22 is electrically and communicatively coupled to each of user interface 20, electromechanical drive 24, and vacuum source 26 via a communication link, such as for example, wire cabling and/or printed circuit traces. Controller circuit 22 may include, for example, a microprocessor circuit 22-1 and an electronic memory circuit 22-2. Controller circuit 22 is configured to execute program instructions to communicate with user interface 20, and is configured to execute program instructions to control electromechanical drive 24 and vacuum source 26 to perform functions associated with the collection of biopsy tissue samples during a biopsy procedure.

Electromechanical drive 24 is drivably coupled (illustrated by a dashed line at the 24/38 interface) to the biopsy probe assembly 14 and is drivably coupled to vacuum source 26 (illustrated by a dashed line between 24 and 26), to selectively and operatively control biopsy probe assembly 14 and vacuum source 26. Electromechanical drive 24 may include, for example, one or more of a linear drive that converts rotational motion to linear motion (e.g., a worm gear arrangement, rack and pinion arrangement, solenoid-slide arrangement, etc.) and a rotational drive that may include one or more of a gear, gear train, belt/pulley arrangement, etc., for effecting operation of biopsy probe assembly 14 and/or vacuum source 26.

Vacuum source 26 may be, for example, a peristaltic pump, a diaphragm pump, syringe-type pump, etc. Vacuum source 26 may be integrated into driver assembly 12. Alternatively, vacuum source 26 may be integrated as a part of the biopsy probe assembly 14. In the present embodiment, vacuum source 26 is configured to generate negative pressure (vacuum).

Sample receptacle 28 is coupled in sealing engagement with, and in fluid communication with, each of biopsy probe assembly 14 and vacuum source 26 to define a fluid path 32, represented by dashed lines, between biopsy probe assembly 14 and vacuum source 26. Sample receptacle 28 is coupled in fluid communication with vacuum source 26 via a conduit 33. Sample collection container 30, which is removably carried by sample receptacle 28, is interposed between biopsy probe assembly 14 and vacuum source 26, with fluid path 32 passing through sample collection container 30.

Biopsy probe assembly 14 is releasably attached to driver assembly 12. Biopsy probe assembly 14 is intended for use on a single patient, and thus is disposed of after use. Biopsy probe assembly 14 includes a frame 34, a biopsy probe 36, and a probe drive 38. Biopsy probe 36 includes an elongate sample receiving member 40 and a cutting cannula 42 operably coupled to probe drive 38.

In the present embodiment, probe drive 38 includes at least one gear connected to each of sample receiving member 40 and a cutting cannula 42 to effect respective rotational movement of each of sample receiving member 40 and cutting cannula 42. In addition, probe drive 38 includes a worm gear to facilitate longitudinal movement of cutting cannula 42 relative to sample receiving member 40. Probe drive 38 is drivably engaged with electromechanical drive 24 of driver assembly 12 when biopsy probe assembly 14 is attached to driver assembly 12.

Sample receiving member 40 and cutting cannula 42 are mounted as a coaxial unit to frame 34. Sample receiving member 40 and cutting cannula 42 are arranged coaxially with respect to a longitudinal axis 44, and are movable relative to one another along longitudinal axis 44. In the embodiment of FIG. 1, sample receiving member 40 is positioned within lumen 42-1 of cutting cannula 42, and cutting cannula 42 is axially slidable over the outer surface of sample receiving member 40. Alternatively, it is contemplated that the coaxial arrangement may be constructed having cutting cannula 42 re-sized and positioned in lumen 40-4 of sample receiving member 40 for axial sliding movement in lumen 40-4 of sample receiving member 40.

In the present embodiment illustrated in FIG. 1, for example, sample receiving member 40 may include, for example, an elongate cylindrical tube, e.g., a metal tube formed from stainless steel, having a proximal end 40-1, a distal end portion 40-2, a tissue receiving notch 40-3, and a lumen 40-4 (shown by dashed lines). Tissue receiving notch 40-3 is formed in the side wall of the elongate cylindrical tube, e.g., by cutting away a portion of the side wall, so as to expose a distal portion of lumen 40-4. A piercing tip 46 is connected to distal end portion 40-2, distal to tissue receiving notch 40-3, to close off distal end portion 40-2. Lumen 40-4 extends from tissue receiving notch 40-3 to proximal end 40-1 and is sealably connected to the removable sample receptacle 28, e.g., by an O-ring or rubber sleeve, so as to extend fluid path 32 to tissue receiving notch 40-3.

Cutting cannula 42 may be a cylindrical tube, e.g., a metal tube formed from stainless steel, having a lumen 42-1 and a distal cutting edge 42-2. In the present embodiment, sample receiving member 40 is positioned in lumen 42-1 of cutting cannula 42, such that cutting cannula 42 slides longitudinally over sample receiving member 40, and is rotatable about sample receiving member 40, so as to sever tissue received in tissue receiving notch 40-3.

Piercing tip 46 is a sharpened tip configured to penetrate tissue to position tissue receiving notch 40-3 at the biopsy site. Tissue receiving notch 40-3 is configured to receive the tissue to be biopsied, and to collect the tissue sample cut from the tissue by cutting cannula 42 during a biopsy procedure.

Figure 2:
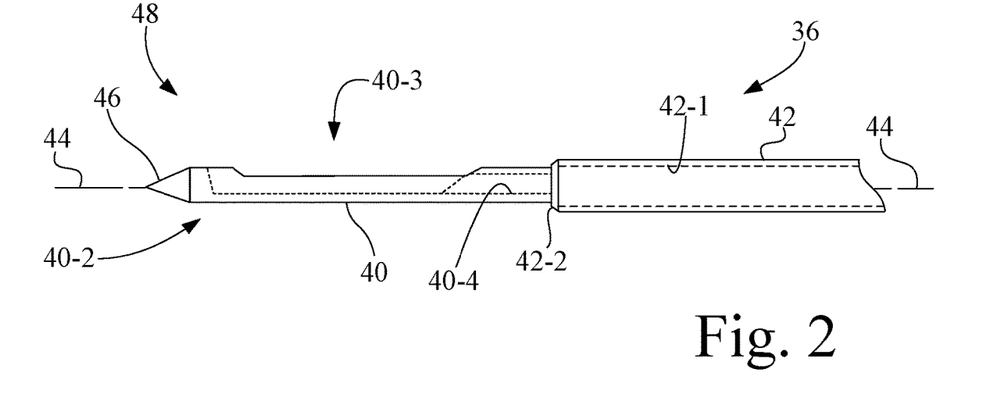
FIG. 2 is a side view of a portion of a biopsy probe assembly of the biopsy apparatus of FIG. 1, having a sample receiving member and a cutting cannula, and with the cutting cannula retracted to an open position so as to expose the tissue receiving notch of the sample receiving member.
Figure 3:
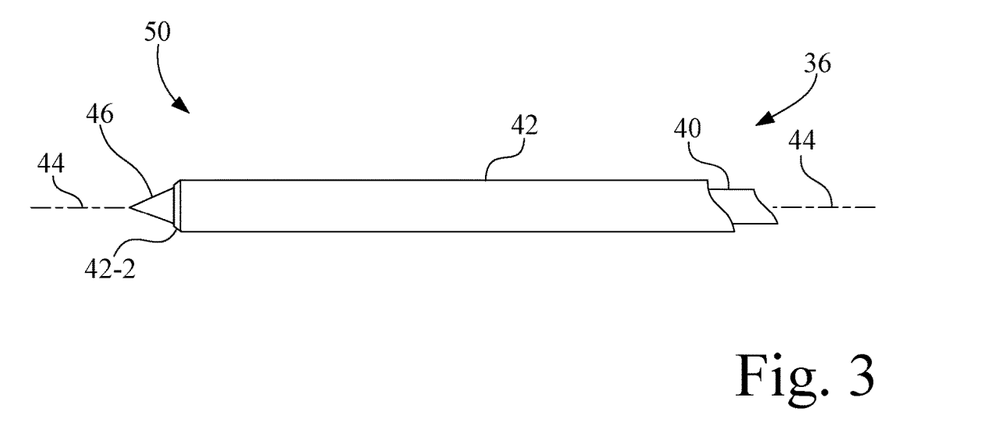
FIG. 3 is a side view of a portion of a biopsy probe assembly of the biopsy apparatus of FIGS. 1 and 2, wherein the cutting cannula is moved over the tissue receiving notch of the sample receiving member to an extended position so as to cover the tissue receiving notch.

Referring also to FIGS. 2 and 3, sample receiving member 40 and cutting cannula 42 are movable relative to one another along longitudinal axis 44 between a first relative position 48 (FIG. 2) and a second relative position 50 (FIG. 3). Referring to FIG. 2, in first relative position 48, cutting cannula 42 is retracted to an open position so as to expose tissue receiving notch 40-3 of sample receiving member 40, such that sample receiving member 40 may receive tissue to be biopsied. Vacuum may be applied before, or during, the retraction of cutting cannula 42 by activation of vacuum source 26, so as to pull tissue that is in the vicinity of tissue receiving notch 40-3 into tissue receiving notch 40-3.

Referring to FIG. 3, in second relative position 50, cutting cannula 42 is moved over tissue receiving notch 40-3 to an extended position so as to cover tissue receiving notch 40-3 of sample receiving member 40. Thus, when cutting cannula 42 is moved over tissue receiving notch 40-3 to cover tissue receiving notch 40-3, any tissue present in tissue receiving notch 40-3 is severed by distal cutting edge 42-2 of cutting cannula 42, and the cut tissue sample is received in lumen 40-4 of sample receiving member 40 adjacent tissue receiving notch 40-3.

Referring again to FIG. 1, vacuum applied by vacuum source 26 will then transport the tissue sample through lumen 40-4 of sample receiving member 40 and expel the tissue sample from proximal end 40-1 of sample receiving member 40 into sample collection container 30.

Figure 4A:
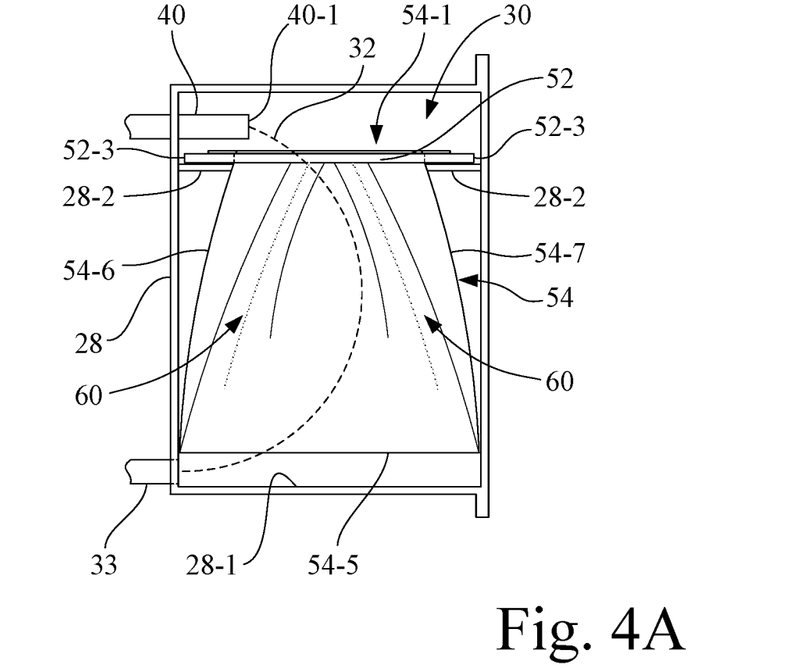
FIG. 4A is a side view of a sample receptacle of the biopsy apparatus of FIG. 1, with the sample receptacle carrying a sample collection container configured in accordance with an aspect of the present invention, and with a sample capture body of the sample collection container in an assembled state.
Figure 4B:
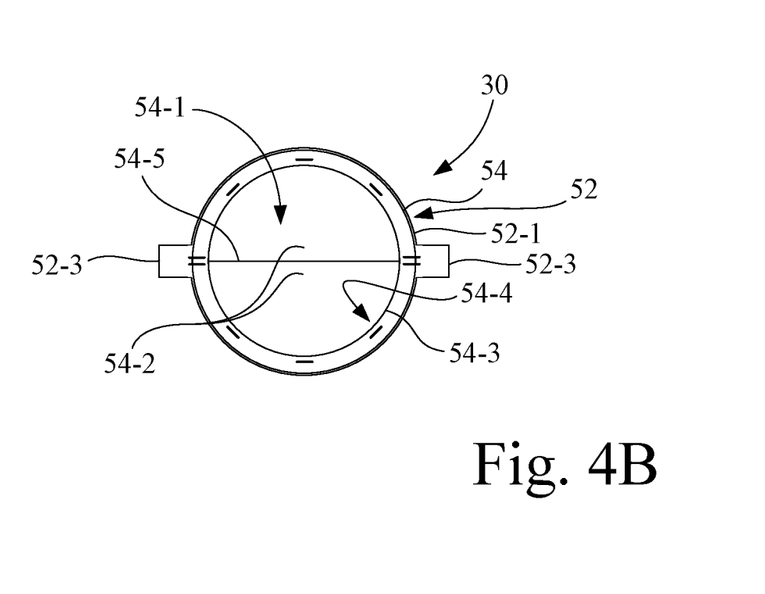
FIG. 4B is a top view of the sample collection container of FIG. 4A having a frame and a sample capture body in accordance with an aspect of the present invention.

FIGS. 4A and 4B show an embodiment of sample collection container 30 configured in accordance with an aspect of the present invention. In the present embodiment, sample collection container 30 is side-loaded into sample receptacle 28, and is suspended above a floor 28-1 of sample receptacle 28 by a support ledge 28-2 that projects inwardly from the inner side walls of sample receptacle 28.

Referring to FIGS. 4A and 4B, sample collection container 30 includes a frame 52 and a sample capture body 54. Frame 52 may be made of plastic or metal. Sample capture body 54 is made of a fabric, such as a polypropylene woven fabric. The fabric is a finely woven fabric to prevent microcalcifications from passing through the fabric.

Figures 5, 6A, 6B:
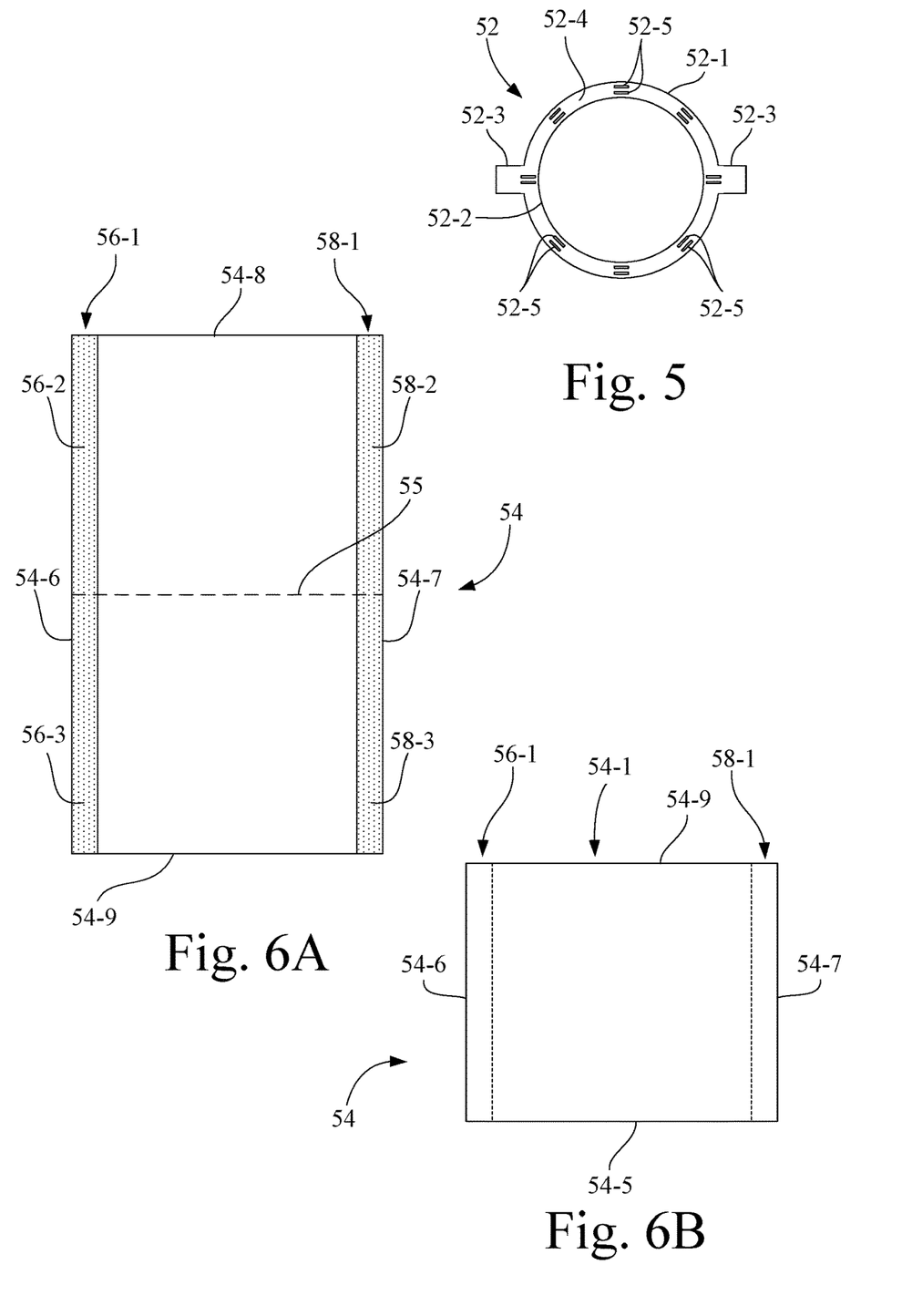
FIG. 5 is a top view of the frame of FIG. 4B having a plurality of mechanical fasteners.
FIG. 6A is a depiction of the rectangular pre-assembly shape of the sample capture body of FIGS. 4A and 4B.
FIG. 6B is a depiction of an intermediate assembly shape of the sample capture body of FIGS. 4A and 4B, wherein the rectangular pre-assembly shape of FIG. 6A is folded along a fold line and adhesively attached at opposing end surface portions.

Sample capture body 54 is removably attached to frame 52. Sample capture body 54, when assembled, defines an interior space 54-1 that is held open when sample capture body 54 is attached to frame 52. Sample capture body 54 has an interior sample capture surface 54-2 that at least partially surrounds interior space 54-1, and in the present embodiment, defines an opening 54-3 at an upper portion 54-4 of interior space 54-1. In the present embodiment, the fabric has a single fold (pleat) 54-5 (see FIG. 4A) formed at a fold line 55 (see FIG. 6).

Referring also to FIG. 5, in the present embodiment, frame 52 is an annular member 52-1 having a frame opening 52-2, and has at least two mounting protrusions, referenced as a group as mounting protrusions 52-3, that extend outwardly from annular member 52-1. Referring again to FIG. 4A, mounting protrusions 52-3 are positioned to engage support ledge 28-2 of sample receptacle 28 to suspend sample capture body 54 above floor 28-1 of sample receptacle 28. Annular member 52-1 has a mounting surface 52-4 that surrounds frame opening 52-2.

Mounting surface 52-4 has a releasable attachment device configured to releasably attach to the fabric of sample capture body 54. The releasable attachment device may be, for example, a non-permanent adhesive, or mechanical fasteners 52-5. In the present embodiment, the mechanical fasteners 52-5 are located around frame opening 52-2, e.g., near frame opening 52-2, and are in the form of a plurality of pinch-points configured to attach to the fabric of sample capture body 54. The pinch-points forming mechanical fasteners 52-5 may be, for example, a plurality of slots into which the fabric of sample capture body 54 is forced, e.g., by poking with a narrow blunt instrument. Alternatively, each of mechanical fasteners 52-5 may be formed as a burr protrusion, e.g., to form a plurality of pairs of barbs, that projects away from mounting surface 52-4 of annular member 52-1 so as to engage, e.g., by snagging, the fabric of sample capture body 54.

In the embodiment of FIGS. 4-6B, sample capture body 54 has an assembly shape (FIG. 4), an intermediate assembly shape (FIG. 6B) and a pre-assembly shape (FIG. 6A). In the present embodiment, referring to FIG. 6A, sample capture body 54 has a rectangular pre-assembly shape having a first side edge 54-6, a second side edge 54-7, a third side edge 54-8, and a fourth side edge 54-9. First side edge 54-6 is orthogonal to third side edge 54-8 and fourth side edge 54-9. Second side edge 54-7 is orthogonal to third side edge 54-8 and fourth side edge 54-9, and second side edge 54-7 is laterally spaced apart from first side edge 54-6.

The rectangular pre-assembly shape of the fabric of sample capture body 54 has a first end surface portion 56-1 that is adjacent first side edge 54-6. First end surface portion 56-1 is divided at fold line 55 to define a first attachment surface portion 56-2 and a second attachment surface portion 56-3. A second end surface portion 58-1 is adjacent the second side edge 54-7. Second end surface portion 58-1 is divided at fold line 55 to define a third attachment surface portion 58-2 and a fourth attachment surface portion 58-3. At least one of first attachment surface portion 56-2 and second attachment surface portion 56-3 is coated with a non-permanent adhesive, sometimes also referred to in the art as "repositionable adhesive". Likewise, at least one of third attachment surface portion 58-2 and fourth attachment surface portion 58-3 is coated with the non-permanent adhesive.

Referring to FIGS. 6A and 6B, to form sample capture body 54, the rectangular pre-assembly is folded at fold line 55 to create fold (pleat) 54-5, with first attachment surface portion 56-2 being attached to second attachment surface portion 56-3 by adhesive, and with third attachment surface portion 58-2 being attached to fourth attachment surface portion 58-3 by adhesive, and wherein third side edge 54-8 and fourth side edge 54-9 are oriented to form opening 54-3 at the upper portion of interior space 54-1. Advantageously, in the assembly shape depicted in FIG. 4, the fabric of sample capture body 54 having pleat 54-5 forms an upwardly extending V-shape that will tend to consolidate, i.e., funnel, tissue particles of a collected tissue sample to pleat 54-5.

To assemble sample collection container 30, the end portion of sample capture body 54 having third side edge 54-8 and fourth side edge 54-9, i.e. opposite to fold line 55, is threaded through opening 52-2 of annular member 52-1, and in doing so, the fabric is bunched, thus forming a plurality of side undulations 60 (see FIG. 4A) along the sides of sample capture body 54. The portion of sample capture body 54 that extends through opening 52-2 of annular member 52-1 is folded over to engage the plurality of mechanical fasteners 52-5 of mounting surface 52-4 of annular member 52-1 of frame 52.

A method of collecting a tissue sample using biopsy apparatus 10 having sample collection container 30 is described as follows. A biopsy is performed using biopsy apparatus 10 to receive a tissue sample and to deliver the received tissue sample, via vacuum assisted transportation, to the sample collection container 30. Advantageously, the V-shape of the fabric of sample capture body 54 that extends upwardly from pleat 54-5 tends to consolidate, i.e., funnel, tissue particles of the collected tissue sample to pleat 54-5. Sample collection container 30 containing the tissue sample is removed from biopsy apparatus 10. Sample capture body 54 is then removed, i.e., detached, from frame 52. Then, the pleated fabric forming sample capture body 54 is unfolded by separating the adhesion at first end surface portion 56-1 and second end surface portion 58-1 so as to facilitate removal of the consolidated tissue particles associated with the received tissue sample from interior sample capture surface 54-2 e.g. near pleat 54-5.

If desired, sample collection container 30 can be reassembled by reversing the disassembly process to permit reuse of the current frame 52 and sample capture body 54, and then reinstalled into biopsy apparatus 10 for collection of a next tissue sample. Alternatively, sample collection container 30 may be reassembled using the current frame 52 and a new sample capture body 54.

Figure 7:
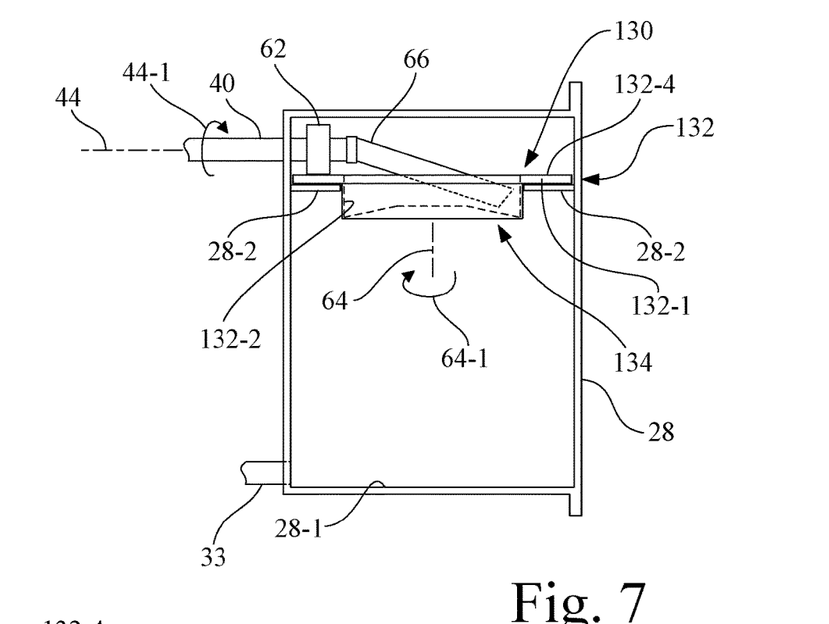
FIG. 7 is a side view of a sample receptacle of the biopsy apparatus of FIG. 1, with the sample receptacle carrying a sample collection container configured in accordance with another embodiment of an aspect of the present invention, and with a sample capture body of the sample collection container in an assembled state.

FIG. 7 shows an embodiment of a sample collection container 130 configured in accordance with an aspect of the present invention. In the present embodiment, sample collection container 130 is side-loaded into sample receptacle 28, and is suspended above a floor 28-1 of sample receptacle 28 by a support ledge 28-2 that projects inwardly from the inner side walls of sample receptacle 28.

Figure 8:
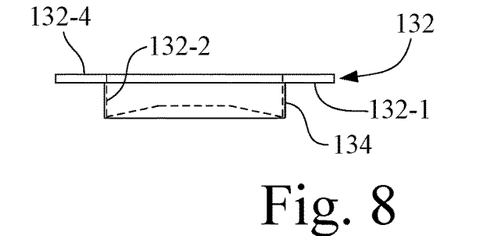
FIG. 8 is a side view of the sample collection container of FIG. 7, removed from the sample receptacle of FIG. 7, and with the sample collection container having a frame attached to the sample capture body.
Figure 9:
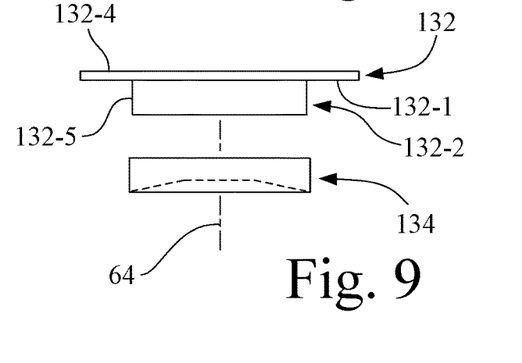
FIG. 9 is an exploded view of the sample collection container of FIG. 8, showing the frame separated from the sample capture body, and with the sample capture body in an assembled state.
Figure 10:
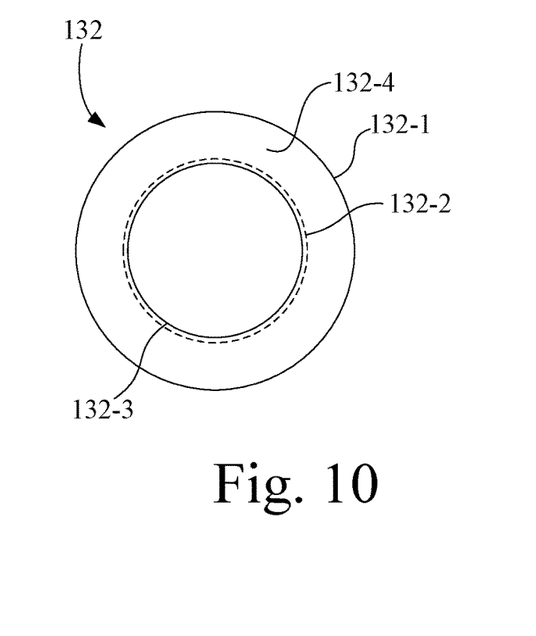
FIG. 10 is a top view of the frame of FIG. 9.

Referring also to FIGS. 8-10, sample collection container 130 includes a frame 132 and a sample capture body 134. Frame 132 may be made of plastic or metal. Sample capture body 134 is made of a fabric, such as a polypropylene woven fabric. The fabric is a finely woven fabric to prevent microcalcifications from passing through the fabric.

Frame 132 includes an annular member 132-1, and a cylindrical sleeve 132-2 that is joined to annular member 132-1. Annular member 132-1 and cylindrical sleeve 132-2 define a frame opening 132-3. Annular member 132-1 has a drive surface 132-4. Cylindrical sleeve 132-2 has a mounting surface 132-5 for mounting sample capture body 134.

Mounting surface 132-5 has a releasable attachment device configured to releasably attach to the fabric of sample capture body 134. The releasable attachment device may be, for example, a non-permanent adhesive, or a mechanical fastener. The mechanical fastener may be configured to include mechanical fasteners, such as mechanical fasteners 52-5 described above with respect to the embodiment of FIG. 5, so as to engage, e.g., by snagging, the fabric of sample capture body 134.

In accordance with the present embodiment, biopsy apparatus 10 further includes a rotational drive 62 for applying a driving force to drive surface 132-4 of annular member 132-1 of frame 132 of sample collection container 130 so as to effect a one-to-one rotational correspondence between the incremental (indexed) rotation of tissue receiving notch 40-3 of sample receiving member 40 about longitudinal axis 44 (e.g., in rotational direction 44-1) and the rotation of sample collection container 130 about rotational axis 64 (e.g., rotational direction 64-1). (See also FIG. 1). As such, as tissue receiving notch 40-3 of sample receiving member 40 is indexed, e.g., through a plurality of angular positions about longitudinal axis 44, by operation of controller circuit 22 and electromechanical drive 24, sample collection container 130 is indexed by rotational drive 62 to corresponding angular positions so as to segregate and identify tissue samples collected at each specific angular position of tissue receiving notch 40-3 of sample receiving member 40.

The application of drive force from rotational drive 62 to drive surface 132-4 of annular member 132-1 of frame 132 of sample collection container 130 may be via a friction drive, e.g., a rubber wheel, or a gear drive, having a drive roller or gear fixed to sample receiving member 40. It is to be understood that rotational drive 62 includes appropriate gearing to effect the desired one-to-one rotational correspondence between the incremental (indexed) rotation of tissue receiving notch 40-3 of sample receiving member 40 about longitudinal axis 44 (see also FIG. 1) and the rotation of sample collection container 130 about rotational axis 64 (see FIG. 7).

A cannula extension 66 is slidably received over proximal end 40-1 of sample receiving member 40. Cannula extension 66 is mounted in a fixed relationship to sample receptacle 28, such that sample receiving member 40 is rotatable about longitudinal axis 44 within cannula extension 66, so as to facilitate the rotational positioning of tissue receiving notch 40-3 of sample receiving member 40 at the desired angular position. After severing a tissue sample and with application of vacuum to sample receptacle 28, the severed tissue sample is transported by vacuum through cannula extension 66 to sample collection container 130, with sample collection container 130 being rotationally indexed about rotational axis 64 in unison with the rotational indexing of tissue receiving notch 40-3 of sample receiving member 40 by operation of rotational drive 62.

Figure 11:
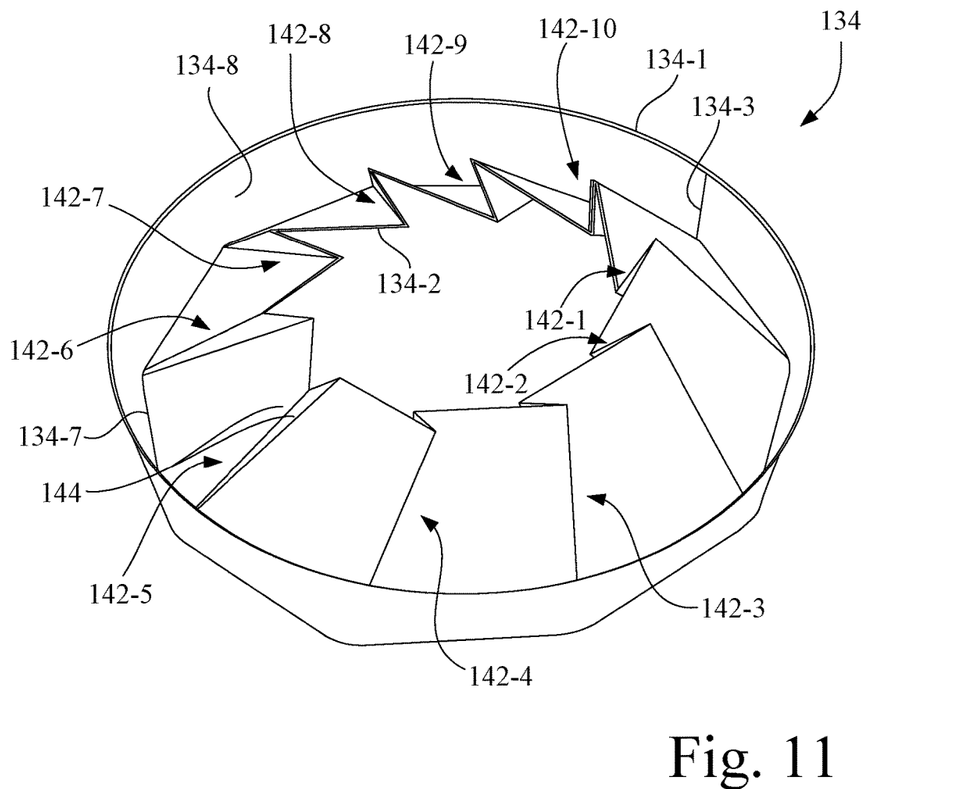
FIG. 11 is an enlarged perspective view of the sample capture body of FIG. 9, and with the sample capture body in an assembled state.
Figure 12:
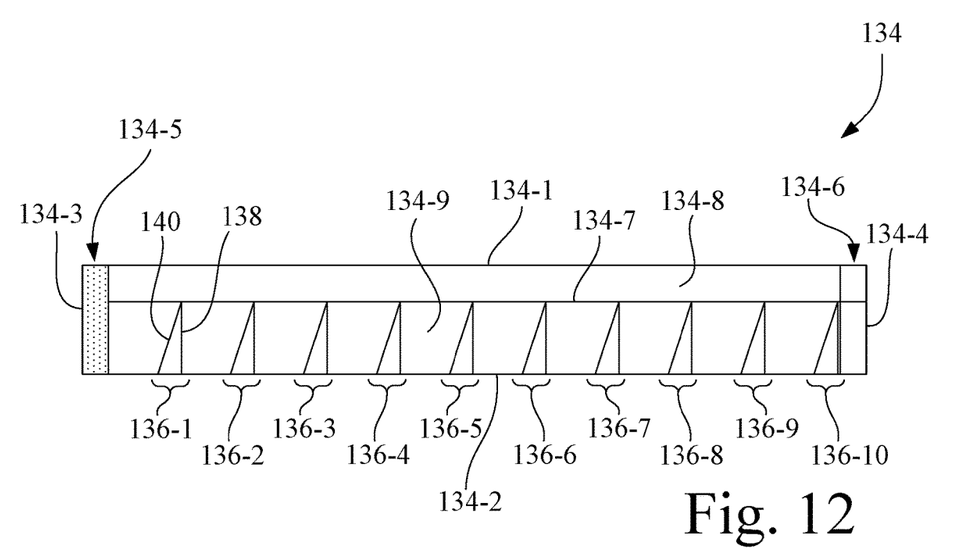
FIG. 12 is a depiction of the rectangular pre-assembly shape of the sample capture body of FIGS. 7-9 and 11, and showing the fold/pleat lines that define fold/pleat locations of the sample capture body.

In the embodiment of FIGS. 7-12, sample capture body 134 has an assembly shape (FIGS. 7, 8, 9, and 11) and a pre-assembly shape (FIG. 12).

In the embodiment of FIGS. 7-12, sample capture body 134 has an assembly shape (FIGS. 7, 8, 9, and 11) and a pre-assembly shape (FIG. 12). In the present embodiment, referring to FIG. 12, sample capture body 134 has a rectangular pre-assembly shape having a first elongate side edge 134-1, a second elongate side edge 134-2, a first lateral edge 134-3, and a second lateral edge 134-4. First elongate side edge 134-1 is orthogonal to first lateral edge 134-3 and second lateral edge 134-4. Also, second elongate side edge 134-2 is orthogonal to the first lateral edge 134-3 and second lateral edge 134-4, and second elongate side edge 134-2 is spaced apart, widthwise, from first elongate side edge 134-1. A first end surface portion 134-5 is adjacent first lateral edge 134-3 and a second end surface portion 134-6 is adjacent the second lateral edge 134-4. One, or both, of first end surface portion 134-5 and second end surface portion 134-6 has a non-permanent adhesive, e.g., a non-permanent adhesive layer.

An elongate fold line 134-7 is defined between first elongate side edge 134-1 and second elongate side edge 134-2. Elongate fold line 134-7 divides the rectangular pre-assembly shape depicted in FIG. 12 into a first region 134-8 between the first elongate side edge 134-1 and the elongate fold line 134-7 and a second region 134-9 between the elongate fold line 134-7 and the second elongate side edge 134-2.

Referring to FIG. 12, a plurality of pairs of pleat lines 136-1, 136-2, 136-3, 136-4, 136-5, 136-6, 136-7, 136-8, 136-9, 136-10 is located in second region 134-9 that respectively define locations of respective pleats (folds) for the assembled sample capture body 134 (see FIG. 11). Each of the plurality of pairs plurality of pairs of pleat lines 136-1, 136-2, 136-3, 136-4, 136-5, 136-6, 136-7, 136-8, 136-9, 136-10 includes a first pleat line 138 and a second pleat line 140. In the present embodiment, each of the pleat lines 138, 140 extends from the elongate fold line 134-7 to the second elongate side edge 134-2, and each pair of pleat lines 138/140 of the plurality of pairs plurality of pairs of pleat lines 136-1, 136-2, 136-3, 136-4, 136-5, 136-6, 136-7, 136-8, 136-9, 136-10 are joined at only one end at elongate fold line 134-7, so as to form a plurality of right-triangular patterns, as depicted in FIG. 12.

During assembly, the rectangular pre-assembly depicted in FIG. 12 is creased at elongate fold line 134-7, and is alternatingly folded at each of the pleat lines 138, 140 to form a plurality of annular structures (see FIG. 11) that define a plurality of sample pockets 142-1, 142-2, 142-3, 142-4, 142-5, 142-6, 142-7, 142-8, 142-9, 142-10 that are arranged in an annular pattern along elongate fold line 134-7, and wherein first end surface portion 134-5 is adhesively attached to second end surface portion 134-6 to complete the assembly of sample capture body 134. In the present embodiment, the plurality of sample pockets 142-1, 142-2, 142-3, 142-4, 142-5, 142-6, 142-7, 142-8, 142-9, 142-10 define a plurality of interior spaces, and with each of the plurality of sample pockets having an interior sample capture surface 144 (see FIG. 11) that at least partially surrounds the respective interior space. In the present embodiment, the plurality of sample pockets 142-1, 142-2, 142-3, 142-4, 142-5, 142-6, 142-7, 142-8, 142-9, 142-10 are arranged to respectively receive tissue samples from each of ten angular positions, e.g., angular positions 1-10, of tissue receiving notch 40-3 of sample receiving member 40 about longitudinal axis 44. It is to be understood that the number of sample pockets may be increased or decreased from that of the present embodiment, if desired.

In the present embodiment, when assembled, sample capture body 134 has a circular side wall at first region 134-8 that transitions at a circular crease (fold) at elongate fold line 134-7 to an annular pleated wall that is formed at second region 134-9. As shown in FIG. 11, the annular pleated wall is oriented at an acute angle at the circular crease at elongate fold line 134-7 with respect to the circular side wall at first region 134-8.

Referring again to FIGS. 7-9, to complete assembly of sample collection container 130, first region 134-8 of the fabric of sample capture body 134 is attached to mounting surface 132-5 of frame 132 by a non-permanent adhesive or mechanical fasteners, so as to form sample collection container 130.

Thus, advantageously, sample capture body 134 may be detached from frame 132 and unfolded to aid in the removal of any tissue sample received by the plurality of sample pockets 142-1, 142-2, 142-3, 142-4, 142-5, 142-6, 142-7, 142-8, 142-9, 142-10 of sample capture body 134, and thereafter, refolded along the fold/pleat lines, reattached to frame 132, and reused to capture additional tissue samples, from the same patient.

As an alternative to the above, it is contemplated that in some embodiments, it may be desirable to use sample capture body 134 in the absence of frame 132.

As a further alternative, it is contemplated that the side structure of either of sample capture body 54 or sample capture body 134 may be reinforced, e.g., via a wire frame, such as a wire spiral, to maintain an open top for receiving tissue samples. Also, it is contemplated that in some embodiments, such reinforcement may be provided in addition to, or in lieu of, the respective frames described above.

The following items also relate to the invention:

In one form, the invention relates to a sample collection container for a biopsy apparatus. In particular, the sample collection container is configured for a biopsy apparatus. The sample collection container includes a sample capture body defining an interior space. The sample capture body is made of a fabric and has an interior sample capture surface that at least partially surrounds the interior space. The fabric may have at least one fold. The fabric may be configured to prevent micro-calcifications from passing through the fabric. In particular, the fabric is a (finely) woven fabric.

Optionally, the sample collection container may include a frame, and the sample capture body may be removably attached to the frame.

In a preferred embodiment, the fabric has a rectangular pre-assembly shape including a first side edge, a second side edge, a third side edge and a fourth side edge. In one implementation, for example, the first side edge is orthogonal to the third side edge and the fourth side edge, and the second side edge is orthogonal to the third side edge and the fourth side edge. The second side edge is laterally spaced apart from the first side edge. A first end surface portion is adjacent the first side edge. The first end surface portion is divided at a fold line to define a first attachment surface portion and a second attachment surface portion. A second end surface portion is adjacent the second side edge. The second end surface portion is divided at the fold line to define a third attachment surface portion and a fourth attachment surface portion. The rectangular pre-assembly folds at the fold line to create a fold, with the first attachment surface portion being attached to the second attachment surface portion by adhesive, and with the third attachment surface portion being attached to the fourth attachment surface portion by adhesive, and wherein the third side edge and the fourth side edge are oriented to form an opening.

A variation may include a frame. The frame may be an annular member having a mounting surface that surrounds a frame opening. The annular surface may have a mechanical fastener, optionally a plurality of mechanical fasteners around the frame opening that is/are configured to attach to the fabric. In one implementation, for example, each of the plurality of mechanical fasteners may be a slot formed in the mounting surface. In another implementation, for example, each of the plurality of mechanical fasteners may be a burr protrusion that projects away from the mounting surface to engage the fabric.

In any of the preceding variations, the fabric may have at least one or a plurality of side undulations.

Further, the fabric may have a plurality of pleats. For example, the plurality of pleats may be arranged in an annular pattern.

In one implementation, the sample capture body may have a circular side wall that transitions at a circular crease to an annular pleated wall. The annular pleated wall may be oriented at an acute angle at the crease with respect to the circular side wall. The annular pleated wall may have a plurality of pleats that form a plurality of cavities, with the plurality of cavities being arranged in an annular pattern.

The fabric of the sample collection container may have a rectangular pre-assembly shape that includes a first elongate side edge, a second elongate side edge, a first lateral edge, and a second lateral edge. In one implementation, for example, the first elongate side edge is orthogonal to the first lateral edge and the second lateral edge, and second elongate side edge is orthogonal to the first lateral edge and the second lateral edge. The second elongate side edge is spaced apart from the first elongate side edge. A first end surface portion is adjacent the first lateral edge and a second end surface portion is adjacent the second lateral edge, wherein at least one of the first end surface portion and the second end surface portion has a non-permanent adhesive. An elongate fold line is defined between the first elongate side edge and the second elongate side edge. The elongate fold line divides the rectangular pre-assembly shape into a first region between the first elongate side edge and the elongate fold line and a second region between the elongate fold line and the second elongate side edge. A plurality of pairs of pleat lines is located in the second region, wherein each pleat line extends from the elongate fold line to the second side edge. Each pair of pleat lines is joined at only one end at the elongate fold line to form a triangular pattern. The rectangular pre-assembly is creased at the elongate fold line and is alternatingly folded at each of the pleat lines to form an annular structure. The first end surface portion may be adhesively attached to the second end surface portion.

The first region of the fabric of the sample capture body may be attached to a frame by a non-permanent adhesive or a mechanical fastener.

The invention also relates to a biopsy apparatus. The biopsy apparatus includes a driver assembly that includes a housing having a proximal end. A vacuum source may be contained within the housing. A biopsy probe assembly is releasably mounted to the housing. The biopsy probe has an elongate sample receiving member and a cutting cannula coaxial with the elongate sample receiving member. A sample receptacle may be removably mounted to the proximal end of the housing. The sample receptacle is coupled in fluid communication with each of the biopsy probe assembly and the vacuum source. A sample collection container is removably carried by the sample receptacle. The sample collection container includes a sample capture body defining an interior space. The sample capture body is made of a fabric and has an interior sample capture surface that at least partially surrounds the interior space. The fabric has at least one fold. The sample collection container may be configured in accordance with any one of the previously described embodiments, implementations, and/or variations thereof.

The invention also relates to the use of a sample collection container in a biopsy apparatus. For example, the invention relates to the use of a sample collection container for a biopsy apparatus, the sample collection container comprising a sample capture body defining an interior space, the sample capture body being made of a fabric and having an interior sample capture surface that at least partially surrounds the interior space, the fabric having at least one fold, wherein the biopsy apparatus comprises a driver assembly that includes a housing having a proximal end; a vacuum source contained within the housing; a biopsy probe assembly releasably mounted to the housing, the biopsy probe having an elongate sample receiving member and a cutting cannula coaxial with the elongate sample receiving member; and a sample receptacle removably mounted to the proximal end of the housing, the sample receptacle being coupled in fluid communication with each of the biopsy probe assembly and the vacuum source; wherein the sample collection container is removably carried by the sample receptacle. The sample collection container may be configured in accordance with any of the previously described embodiments, implementations and/or variations thereof.

As used herein, relative modifiers, such as "near", and other words of degree are intended to indicate permissible variation from the characteristic so modified. It is not intended to be limited to the absolute value or characteristic which it modifies but rather possessing more of the physical or functional characteristic than its opposite, and approaching or approximating such a physical or functional characteristic.

While this invention has been described with respect to multiple embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A sample collection container for a biopsy apparatus, comprising a sample capture body defining an interior space, the sample capture body being made of a fabric and having an interior sample capture surface that at least partially surrounds the interior space, the fabric having a fold, the sample capture body having a pair of opposed surfaces that extend from the fold to form a V-shape of the fabric; and
   a frame, the sample capture body being removably attached to the frame, wherein the frame is an annular member having a mounting surface that defines a frame opening, the annular surface having a plurality of mechanical fasteners around the frame opening that are configured to attach to the fabric.

2. The sample collection container of claim 1, wherein the fabric has a rectangular pre-assembly shape comprising:
   a first side edge, a second side edge, a third side edge and a fourth side edge, the first side edge being orthogonal to the third side edge and the fourth side edge, and the second side edge being orthogonal to the third side edge and the fourth side edge, and the second side edge being laterally spaced apart from the first side edge;
   a first end surface portion adjacent the first side edge, the first end surface portion being divided at a fold line to define a first attachment surface portion and a second attachment surface portion; and
   a second end surface portion adjacent the second side edge, the second end surface portion being divided at the fold line to define a third attachment surface portion and a fourth attachment surface portion;
   wherein the rectangular pre-assembly folds at the fold line to create the fold, with the first attachment surface portion being attached to the second attachment surface portion by adhesive, and with the third attachment surface portion being attached to the fourth attachment surface portion by adhesive, and wherein the third side edge and the fourth side edge being oriented to form an opening.

3. The sample collection container of claim 1, wherein each of the plurality of mechanical fasteners is a slot formed in the mounting surface.

4. The sample collection container of claim 1, wherein each of the plurality of mechanical fasteners is a burr protrusion that projects away from the mounting surface to engage the fabric.

5. The sample collection container of claim 4, wherein the fabric has a plurality of side undulations.

6. The sample collection container of claim 1, wherein the fabric has a plurality of side undulations.

7. The sample collection container of claim 1, wherein the frame opening is positioned to allow a sample to be passed therethrough.

8. The sample container of claim 1, wherein the pair of opposed surfaces are releasably adhered to one another to define the interior space.

9. A sample collection container for a biopsy apparatus, comprising a sample capture body having a circular side wall that transitions at a circular crease to an annular pleated wall comprised of a plurality of individual pleats and defining an interior space, the sample capture body being made of a fabric and having an interior sample capture surface that at least partially surrounds the interior space.

10. The sample collection container of claim 9, wherein the plurality of individual pleats are arranged in an annular pattern.

11. The sample collection container of claim 9, wherein the annular pleated wall is oriented at an acute angle at the crease with respect to the circular side wall.

12. The sample collection container of claim 11, wherein the plurality of individual pleats form a plurality of cavities, the plurality of cavities being arranged in an annular pattern.

13. The sample collection container of claim 9, wherein the plurality of individual pleats form a plurality of cavities, the plurality of cavities being arranged in an annular pattern.

14. A biopsy apparatus, comprising:
a driver assembly that includes a housing having a proximal end;
a vacuum source contained within the housing;
a biopsy probe assembly releasably mounted to the housing, the biopsy probe having an elongate sample receiving member and a cutting cannula coaxial with the elongate sample receiving member;
a sample receptacle removably mounted to the proximal end of the housing, the sample receptacle being coupled in fluid communication with each of the biopsy probe assembly and the vacuum source; and
a sample collection container removably carried by the sample receptacle, the sample collection container including a sample capture body defining an interior space, the sample capture body constructed of a fabric and having an interior sample capture surface that at least partially surrounds the interior space, the fabric having at least one fold; and
a frame, the sample capture body being removably attached to the frame, wherein the frame is an annular member having a mounting surface that defines a frame opening, the annular surface having a plurality of mechanical fasteners around the frame opening that are configured to attach to the fabric.

15. The biopsy apparatus of claim 14, wherein the at least one fold is a single fold that defines a V-shape of the fabric of the sample capture body.

16. The biopsy apparatus of claim 14, wherein the fabric of the sample capture body has a plurality of pleats.

* * * * *